United States Patent
Iwama et al.

(10) Patent No.: US 8,906,969 B2
(45) Date of Patent: *Dec. 9, 2014

(54) PROCESS FOR PRODUCING HYDROCARBON OIL AND SYSTEM FOR PRODUCING HYDROCARBON OIL

(75) Inventors: Marie Iwama, Tokyo (JP); Kazuhiko Tasaka, Tokyo (JP); Yuichi Tanaka, Tokyo (JP)

(73) Assignees: Japan Oil, Gas, and Metals National Corporation, Tokyo (JP); Inpex Corporation, Tokyo (JP); JX Nippon Oil & Energy Corporation, Tokyo (JP); Japan Petroleum Exploration Co., Ltd., Tokyo (JP); Cosmo Oil Co., Ltd., Tokyo (JP); Nippon Steel & Sumikin Engineering Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/817,247

(22) PCT Filed: Aug. 12, 2011

(86) PCT No.: PCT/JP2011/068481

§ 371 (c)(1),
(2), (4) Date: Feb. 15, 2013

(87) PCT Pub. No.: WO2012/023527

PCT Pub. Date: Feb. 23, 2012

(65) Prior Publication Data

US 2013/0143971 A1    Jun. 6, 2013

(30) Foreign Application Priority Data

Aug. 19, 2010   (JP) .................................. 2010-184085

(51) Int. Cl.
| | |
|---|---|
| *C07C 27/00* | (2006.01) |
| *B01D 12/00* | (2006.01) |
| *C07C 1/04* | (2006.01) |
| *C10G 47/00* | (2006.01) |
| *C10G 2/00* | (2006.01) |
| *B01J 8/00* | (2006.01) |
| *C10G 31/00* | (2006.01) |
| *B01J 8/22* | (2006.01) |

(52) U.S. Cl.
CPC . *C07C 1/04* (2013.01); *C10G 47/00* (2013.01); *C10G 2/00* (2013.01); *B01J 8/007* (2013.01); *C10G 31/00* (2013.01); *C10G 2/342* (2013.01); *B01J 8/22* (2013.01); *C10G 2300/208* (2013.01)
USPC .......................................... 518/700; 210/513

(58) Field of Classification Search
CPC ....................................................... C07C 22/13
USPC ............................................. 518/700; 210/513
See application file for complete search history.

(56) References Cited

U.S. PATENT DOCUMENTS

| | | | |
|---|---|---|---|
| 5,827,903 | A | 10/1998 | White et al. |
| 6,124,367 | A | 9/2000 | Plecha et al. |
| 7,488,760 | B2 | 2/2009 | Vogel |
| 2005/0004239 | A1 | 1/2005 | Bull et al. |
| 2006/0144755 | A1 | 7/2006 | Benazzi et al. |
| 2007/0014703 | A1 | 1/2007 | Schweitzer et al. |
| 2007/0197667 | A1 | 8/2007 | Vogel |
| 2010/0239474 | A1 | 9/2010 | Onishi |
| 2011/0036753 | A1 | 2/2011 | Tasaka |
| 2011/0044859 | A1 | 2/2011 | Onishi et al. |
| 2011/0190403 | A1 | 8/2011 | Onishi et al. |
| 2011/0281960 | A1 | 11/2011 | Tasaka |
| 2013/0144099 | A1 | 6/2013 | Tasaka et al. |

FOREIGN PATENT DOCUMENTS

| | | |
|---|---|---|
| AU | 2009224349 | 9/2009 |
| CA | 2 718 173 | 9/2009 |
| CA | 2 737 881 | 4/2010 |
| CA | 2738043 | 4/2010 |
| CN | 1822896 | 8/2006 |
| CN | 201218256 | 4/2009 |
| EP | 2261306 | 12/2010 |
| JP | 2002-502686 | 1/2002 |
| JP | 2004-323626 A | 11/2004 |
| JP | 2006-22283 A | 1/2006 |
| JP | 2007-530710 | 11/2007 |
| JP | 4340389 | 7/2009 |
| JP | 2009-221299 | 10/2009 |
| JP | 2009-221301 A | 10/2009 |

(Continued)

OTHER PUBLICATIONS

International Preliminary Report on Patentability Application No. PCT/JP2011/068481, mail date is Mar. 28, 2013.
Search report from International Application No. PCT/2011/068481, mail date is Nov. 8, 2011.
International Preliminary Report on Patentability for PCT/JP2011/068476, mailed on Mar. 28, 2013.
Search Report from International Application No. PCT/JP2011/068476, mail date is Oct. 18, 2011.

(Continued)

*Primary Examiner* — Jafar Parsa
(74) *Attorney, Agent, or Firm* — Greenblum & Bernstein, P.L.C.

(57) ABSTRACT

Hydrocarbon oil obtained by Fischer-Tropsch synthesis reaction using a slurry bed reactor holding a slurry of a liquid hydrocarbon in which a catalyst is suspended; the hydrocarbon oil is fractionated into a distilled oil and a column bottom oil containing the catalyst fine powder by a rectifying column; at least part of the column bottom oil is transferred to a storage tank, and the catalyst fine powder is sedimented to the bottom of the storage tank to capture the catalyst fine powder; a residue of the column bottom oil is transferred from the rectifying column to a hydrocracker, and/or the supernatant of the column bottom oil from which the catalyst fine powder is captured by the storage tank is transferred from the storage tank to the hydrocracker; and using the hydrocracker, the residue of the column bottom oil and/or the supernatant of the column bottom oil is hydrocracked.

2 Claims, 4 Drawing Sheets

(56) References Cited

FOREIGN PATENT DOCUMENTS

| JP | 2009-221305 | 10/2009 |
|----|-------------|---------|
| WO | 99/39825 | 8/1999 |
| WO | 2009/041600 A1 | 4/2009 |
| WO | 2009/113613 A1 | 9/2009 |
| WO | 2010/038400 A1 | 4/2010 |

OTHER PUBLICATIONS

Search Report for EP Patent Application No. 11818169.2, which was mailed on Apr. 1, 2014.
Office Action for Chinese Patent Application No. 201180050338.2, which was mailed on Mar. 31, 2014.
Office Action for U.S. Appl. No. 13/817,182, dated Aug. 14, 2014.

Fig.4
(a)
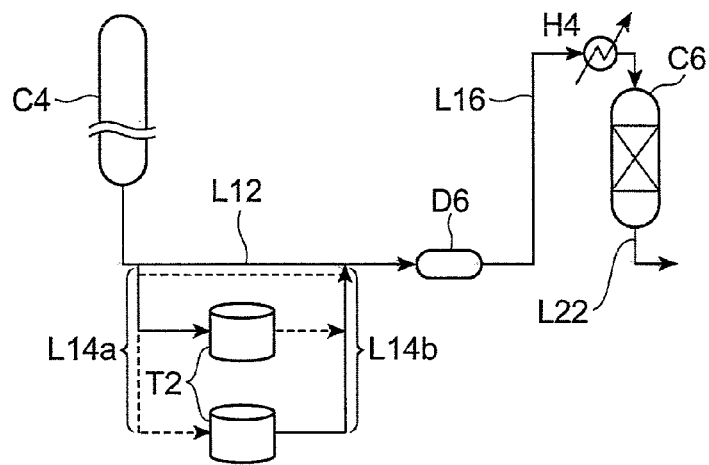
(b)
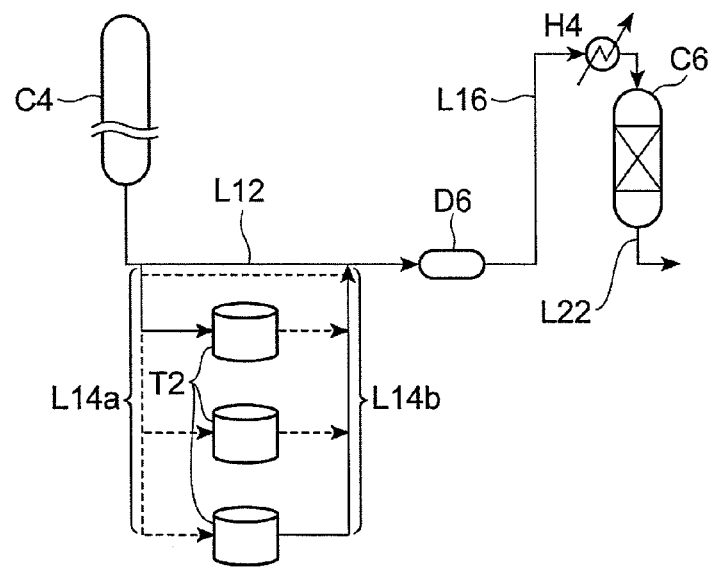
→ LINE IN WHICH FLUID FLOWS
---▶ CLOSED LINE
→/---▶ LINE IN WHICH FLUID FLOWS, OR CLOSED LINE

PROCESS FOR PRODUCING HYDROCARBON OIL AND SYSTEM FOR PRODUCING HYDROCARBON OIL

TECHNICAL FIELD

The present invention relates to a method for producing a hydrocarbon oil and a system for producing a hydrocarbon oil.

BACKGROUND ART

Recently, from the viewpoint of reduction in environmental load, clean and eco-friendly liquid fuels in which the contents of sulfur and aromatic hydrocarbons are small have been demanded. From such a viewpoint, as a technique for producing a raw material hydrocarbon in order to produce a fuel oil base material that contains no sulfur or aromatic hydrocarbons and is rich in aliphatic hydrocarbons, particularly, a kerosene and light oil base material, a method using a Fischer-Tropsch synthesis reaction (hereinafter, referred to as the "FT synthesis reaction" in some cases) in which carbon monoxide gas and hydrogen gas are used as the raw material has been examined.

Moreover, a technique in which a synthesis gas whose principal component is carbon monoxide gas and hydrogen gas is produced by reforming of a gaseous hydrocarbon raw material such as natural gas, a hydrocarbon oil (hereinafter, referred to as the "FT synthetic oil" in some cases) is synthesized from the synthesis gas by the FT synthesis reaction, and further, through an upgrading step that is a step of hydrogenating and refining the FT synthetic oil to produce a variety of liquid fuel oil base materials, the kerosene and light oil base material and naphtha or wax and the like are produced is known as a GTL (Gas To Liquids) process (see the following Patent Literature 1, for example.).

As a synthesis reaction system that synthesizes the hydrocarbon oil by the FT synthesis reaction, for example, a bubble column type slurry bed FT synthesis reaction system that blows a synthesis gas into a slurry, in which a solid catalyst (hereinafter, referred to as the "FT synthesis catalyst" in some cases) particle having activity to the FT synthesis reaction is suspended in the hydrocarbon oil, to make the FT synthesis reaction is disclosed (see Patent Literature 2.).

As a bubble column type slurry bed FT synthesis reaction system, for example, an external circulating system including a reactor that accommodates a slurry to make the FT synthesis reaction, a gas feeder that blows the synthesis gas into a bottom of the reactor, an outflow pipe that evacuates from the reactor the slurry containing the hydrocarbon oil obtained by the FT synthesis reaction within the reactor, a catalyst separator that separates the slurry evacuated through the outflow pipe into the hydrocarbon oil and the FT synthesis catalyst particle, and a re-introducing pipe that re-introduces the FT synthesis catalyst particle and part of the hydrocarbon oil separated by the catalyst separator into the reactor is known.

CITATION LIST

Patent Literature

[Patent Literature 1] Japanese Patent Application Laid-Open Publication No. 2004-323626
[Patent Literature 2] U.S. Patent Application Laid-Open Publication No. 2007/0014703

SUMMARY OF INVENTION

Technical Problem

The catalyst separator in the bubble column type slurry bed FT synthesis reaction system includes a filter whose opening is approximately 10 μm, for example. The FT synthesis catalyst particle in the slurry is captured by the filter to be separated from the hydrocarbon oil.

However, part of the FT synthesis catalyst particles are gradually reduced to a fine powder due to friction between the FT synthesis catalyst particles, friction with an inner wall or the like of the reactor, or thermal damage caused by the FT synthesis reaction. The fine powder whose particle size becomes smaller than the size of the opening of the filter in the catalyst separator (hereinafter, referred to as the "catalyst fine powder" in some cases) may unintendedly pass through the filter with the hydrocarbon oil to flow into a reaction system in the upgrading step of the FT synthetic oil. The flow of the catalyst fine powder into the reaction system causes deterioration in the catalyst used in the reaction system, increase in pressure loss of the reactor, and further, reduction in quality of liquid fuel base materials and liquid fuel products. However, it is difficult to provide a filter having an opening smaller than the particle size of the catalyst fine powder in a flow path in which the FT synthetic oil obtained by the FT synthesis reaction flows at a large flow rate, thereby to capture the catalyst fine powder, because pressure loss in the filter is large, and the pressure loss is further increased by capturing of the catalyst fine powder.

The present invention has been made in consideration of the problems above, and an object of the present invention is to provide a method for producing a hydrocarbon oil and a production system that can suppress a flow of a catalyst fine powder derived from a catalyst to be used for the FT synthesis reaction into a reaction system in an upgrading step.

Solution to Problem

In order to achieve the object above, a method for producing a hydrocarbon oil according to the present invention comprises: a step of obtaining a hydrocarbon oil containing a catalyst fine powder derived from a catalyst by a Fischer-Tropsch synthesis reaction using a slurry bed reactor holding a slurry containing a liquid hydrocarbon and the catalyst suspended in the liquid hydrocarbon within the slurry bed reactor; a step of fractionating the hydrocarbon oil into at least one distilled oil and a column bottom oil containing the catalyst fine powder using a rectifying column; a step of transferring at least part of the column bottom oil to a storage tank, and sedimenting the catalyst fine powder to a bottom of the storage tank to capture the catalyst fine powder; and a step of transferring a residue of the column bottom oil from the rectifying column to a hydrocracker, and/or transferring a supernatant of the column bottom oil in which the catalyst fine powder is captured in the storage tank from the storage tank to the hydrocracker to hydrocrack the residue of the column bottom oil and/or the supernatant of the column bottom oil using the hydrocracker.

According to the method for producing a hydrocarbon oil according to the present invention, the catalyst fine powder contained in the FT synthetic oil is condensed in the column bottom oil of the rectifying column, at least part of the column bottom oil in which the catalyst fine powder is condensed is transferred to the storage tank, and the catalyst fine powder is sedimented to the bottom of the storage tank to be captured; thereby, the flow of the catalyst fine powder into a reaction system (hydrocracker) for hydrocracking of the column bottom oil can be efficiently suppressed.

In the method for producing a hydrocarbon oil according to the present invention, it is preferable that the storage tank include a structure for suppressing movement of the catalyst fine powder sedimented to the bottom of the storage tank in the bottom of the storage tank. Thereby, the flow of the catalyst fine powder into the reaction system (hydrocracker) for hydrocracking of the column bottom oil can be more efficiently suppressed.

A system for producing a hydrocarbon oil according to the present invention includes: a Fischer-Tropsch synthesis reaction apparatus for obtaining a hydrocarbon oil containing a catalyst fine powder derived from a catalyst, the apparatus having a slurry bed reactor holding a slurry containing a liquid hydrocarbon and the catalyst suspended in the liquid hydrocarbon within the slurry bed reactor; a rectifying column for fractionating the hydrocarbon oil at least one distilled oil and a column bottom oil; a hydrocracker for hydrocracking the column bottom oil; a bypass line connecting a column bottom of the rectifying column to the hydrocracker; a transfer line branched from a branching point of the bypass line; and a storage tank that is connected to the transfer line, and in which the catalyst fine powder is sedimented to a bottom to be captured.

The system for producing a hydrocarbon oil according to the present invention can implement the method for producing a hydrocarbon oil according to the present invention.

In the system for producing a hydrocarbon oil according to the present invention, it is preferable that the storage tank include a structure for suppressing movement of the catalyst fine powder sedimented to the bottom of the storage tank in the bottom of the storage tank. Thereby, the flow of the catalyst fine powder into a reaction system (hydrocracker) for hydrocracking of the column bottom oil can be more efficiently suppressed.

Advantageous Effects of Invention

The present invention can provide a method for producing a hydrocarbon oil and a production system that can efficiently suppress the flow of the catalyst fine powder derived from the catalyst to be used for the FT synthesis reaction into the reaction system in the upgrading step of the FT synthetic oil.

BRIEF DESCRIPTION OF DRAWINGS

FIGS. 4(A) and 4(B) are a schematic view showing a specific example of an arrangement of a storage tank that a system for a hydrocarbon oil according to the embodiment of the present invention includes.

DESCRIPTION OF EMBODIMENTS

Figure 1:
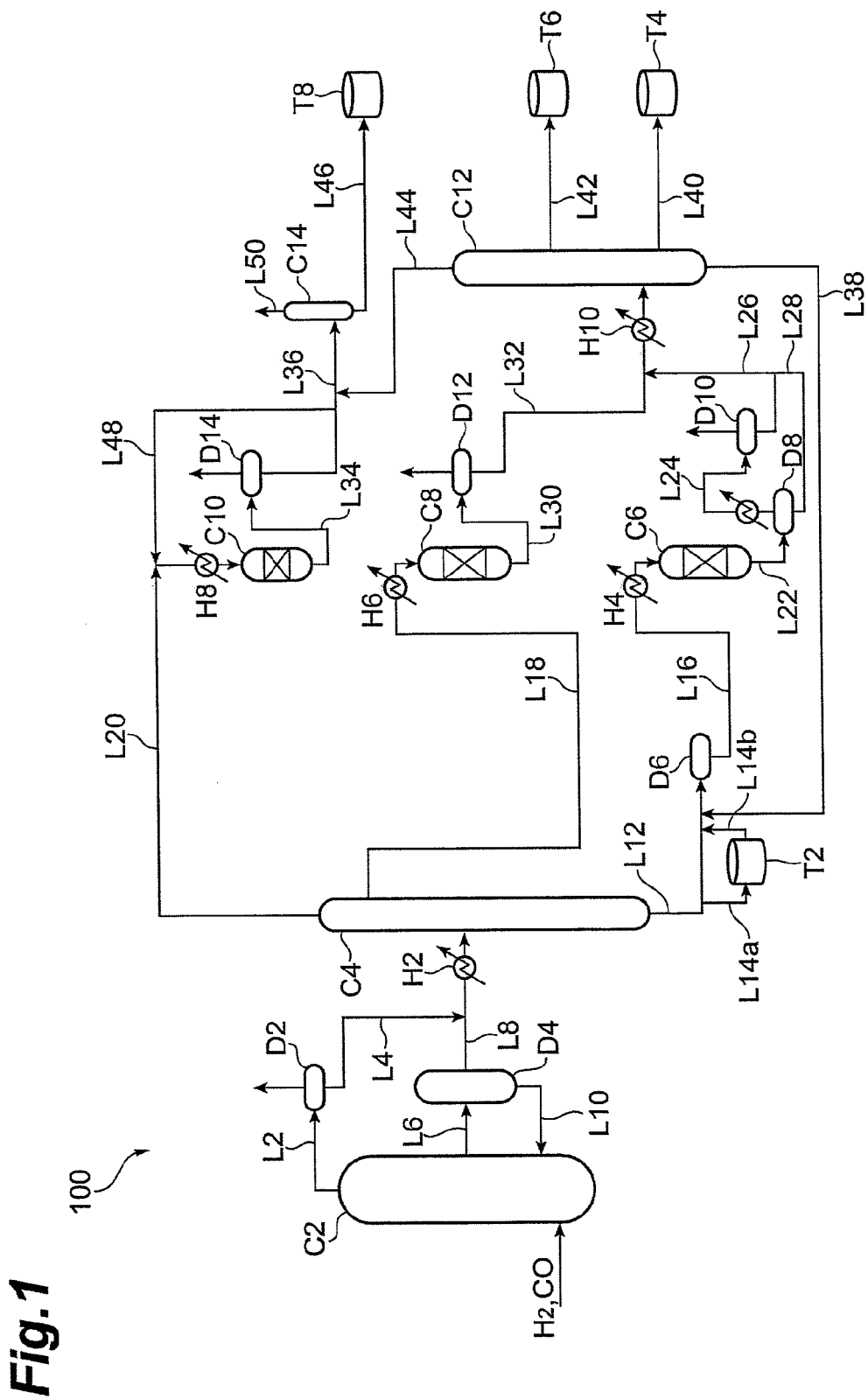
FIG. 1 is a schematic view of an example of a system for producing a hydrocarbon oil according to an embodiment of the present invention.

Hereinafter, with reference to FIGS. 1 to 4, a method for producing a hydrocarbon oil using a system for producing a hydrocarbon oil and a production system according to one embodiment of the present invention will be described in detail. Same reference numerals will be given to same or identical components.

(Outline of System for Producing Hydrocarbon Oil)

A system 100 for producing a hydrocarbon oil used in the present embodiment is a plant facility for performing a GTL process that converts a hydrocarbon raw material such as natural gas into a liquid fuel (hydrocarbon oil) base material such as light oil, kerosene, and naphtha. The system 100 for producing a hydrocarbon oil according to the present embodiment mainly includes a reformer (not shown), a bubble column type slurry bed reactor C2, a first rectifying column C4, bypass lines L12 and L16, transfer lines L14a and L14b (or only L14a in some cases), a storage tank T2, a hydrocracker C6, an intermediate fraction hydrorefining apparatus C8, a naphtha fraction hydrorefining apparatus C10, and a second rectifying column C12. The line L12 that forms the bypass line connects the first rectifying column C4 to a mixing drum D6. The line L16 that forms the bypass line connects a mixing drum D2 to the hydrocracker C6. In FIG. 1, an example in which in the system 100 for producing a hydrocarbon oil, the storage tank T2 is provided between the transfer lines L14a and L14b has been shown; the storage tank T2 may be connected to the transfer line L14a, and the production system 100 may not have the transfer line L14b. In this case, at least part of the crude wax fraction containing the catalyst fine powder flowed from the column bottom of the first rectifying column C4 is fed through the transfer line L14a to the storage tank T2, and the supernatant of the crude wax fraction in which the catalyst fine powder is captured in the storage tank T2 is flowed reversely in the transfer line L14a to be discharged. The "line" means a piping for transferring a fluid.

(Outline of Method for Producing Hydrocarbon Oil)

A method for producing a hydrocarbon oil using the production system 100 comprises the following steps S1 to S9.

In Step S1, in the reformer (not shown), natural gas as the hydrocarbon raw material is reformed to produce a synthesis gas containing carbon monoxide gas and hydrogen gas.

In Step S2, in the bubble column type slurry bed reactor C2, by the FT synthesis reaction using an FT synthesis catalyst, a hydrocarbon oil (FT synthetic oil) is synthesized from the synthesis gas obtained in Step S1. In Step S2, a catalyst fine powder may be produced from part of the FT synthesis catalyst, and part of the catalyst fine powder may pass through the filter, which separates the hydrocarbon oil from the FT synthesis catalyst particles, to be mixed in the FT synthetic oil to be fed to Step S3 described below.

In Step S3, in the first rectifying column C4, the FT synthetic oil obtained in Step S2 is fractionated into at least one distilled oil and a column bottom oil containing the catalyst fine powder. In the present embodiment, by the fractionation, the FT synthetic oil is separated into a crude naphtha fraction, a crude intermediate fraction, and a crude wax fraction. Here, the crude naphtha fraction and crude intermediate fraction are distilled oils each obtained by condensing a product once vaporized from the FT synthetic oil in the first rectifying column C4, and evacuating the products from the column top of the first rectifying column C4 and the column middle thereof, respectively; the crude wax fraction is a column bottom oil evacuated as it is a liquid from the column bottom without vaporization from the FT synthetic oil. The column bottom oil may contain the catalyst fine powder produced in Step S2 and mixed in the FT synthetic oil. The crude naphtha fraction, the crude intermediate fraction, and the crude wax fraction each refer to a fraction obtained by fractionation of the FT synthetic oil and not subjected to a hydrorefining or hydrocracking treatment.

The steps subsequent to Step S4 to be described below comprise the upgrading step of the FT synthetic oil.

In Step S4, at least part of the crude wax fraction that is the column bottom oil of the first rectifying column C4 separated in Step S3 and contains the catalyst fine powder is transferred through the line L12 and the transfer line L14a branched from the branching point of the line L12 to the storage tank T2; in the storage tank T2, the catalyst fine powder contained in the crude wax fraction are sedimented to the bottom of the storage tank T2 to be separated and captured; thereby, the catalyst fine powder is removed from the crude wax fraction.

In Step S5, of the crude wax fraction containing the catalyst fine powder and separated in Step S3, the remaining crude wax fraction not transferred to the storage tank T2 in Step S4 is transferred through the lines L12 and L16 that form a bypass line from the first rectifying column C4 to the hydrocracker C6. The supernatant of the crude wax fraction in which in the storage tank T2, the catalyst fine powder is sedimented and separated to be captured at the bottom of the storage tank T2 is transferred through the transfer line L14b (or the line L14a in some cases) and the line L16 from the storage tank T2 to the hydrocracker C6.

In Step S6, in the hydrocracker C6, the crude wax fraction separated in Step 3, subjected to removal of the catalyst fine powder from at least part of the crude wax fraction in Step S4, and transferred in Step S5 is hydrocracked.

In Step S7, in the intermediate fraction hydrorefining apparatus C8, hydrorefining of the crude intermediate fraction is performed.

In Step S8, in the naphtha fraction hydrorefining apparatus C10, hydrorefining of the crude naphtha fraction is performed. Further, the hydrorefined naphtha fraction is fractionated in a naphtha stabilizer C14 to recover naphtha (GTL-naphtha) that is a product of the GTL process.

In Step S9, a mixture of the hydrocracking product of the crude wax fraction and the hydrorefined product of the crude intermediate fraction is fractionated in the second rectifying column C12. By the fractionation, a light oil (GTL-light oil) base material and a kerosene (GTL-kerosene) base material that are products of the GTL process are recovered.

Hereinafter, Steps S1 to S9 will be described more in detail.
(Step S1)

In Step S1, first, a sulfur compound contained in natural gas is removed by a desulfurization apparatus (not shown). Usually, the desulfurization apparatus includes a hydrogenation desulfurization reactor filled with a known hydrogenation desulfurization catalyst and an adsorptive desulfurization apparatus provided at the rear stage thereof and filled with an adsorptive material for hydrogen sulfide such as zinc oxide. The natural gas is fed to the hydrogenation desulfurization reactor with hydrogen, and the sulfur compound in the natural gas is converted into hydrogen sulfide. Subsequently, in the adsorptive desulfurization apparatus, hydrogen sulfide is removed by adsorption, and the natural gas is desulfurized. By the desulfurization of the natural gas, poisoning of a reforming catalyst filled in the reformer, the FT synthesis catalyst used in Step S2, and the like by the sulfur compound is prevented.

The desulfurized natural gas is fed to reforming using carbon dioxide and steam in the reformer to produce a synthesis gas at a high temperature containing carbon monoxide gas and hydrogen gas as principal components. The reforming reaction of the natural gas in Step S1 is represented by reaction equations (1) and (2). The reforming method is not limited to the steam carbon dioxide gas reforming method using carbon dioxide and steam; for example, a steam reforming method, a partial oxidation reforming method (PDX) using oxygen, an autothermal reforming method (ATR) that is a combination of the partial oxidation reforming and the steam reforming method, a carbon dioxide gas reforming method, or the like can also be used.

$$CH_4 + H_2O \longrightarrow CO + 3H_2 \tag{1}$$

$$CH_4 + CO_2 \longrightarrow 2CO + 2H_2 \tag{2}$$

(Step S2)

In Step S2, the synthesis gas produced in Step S1 is fed to the bubble column type slurry bed reactor C2, and hydrocarbon is synthesized from hydrogen gas and carbon monoxide gas in the synthesis gas.

The bubble column type slurry bed FT reaction system including the bubble column type slurry bed reactor C2 mainly includes the bubble column type slurry bed reactor C2 that accommodates a slurry containing the FT synthesis catalyst, a gas feeder that blows the synthesis gas into the bottom of the reactor (not shown), a line L2 that evacuates the gaseous hydrocarbon obtained by the FT synthesis reaction and the non-reacted synthesis gas from the column top of the bubble column type slurry bed reactor C2, a gas liquid separator D2 that cools the gaseous hydrocarbon and non-reacted synthesis gas evacuated from the line L2 and separates them into gas and liquid, an outflow pipe L6 that evacuates the slurry containing hydrocarbon oil from the reactor, a catalyst separator D4 that separates the slurry evacuated through the outflow pipe into the hydrocarbon oil and the FT synthesis catalyst particles, and a re-introducing pipe L10 that re-introduces the FT synthesis catalyst particles and part of the hydrocarbon oil separated by the catalyst separator D4 into the reactor, for example. Inside of the bubble column type slurry bed reactor C2, a heat conducting pipe (not shown) for removing the reaction heat generated by the FT synthesis reaction, through which cool water is flowed, is provided.

As the FT synthesis catalyst used in the bubble column type slurry bed reactor C2, a known carrier type FT synthesis catalyst in which an active metal is supported by an inorganic carrier is used. As the inorganic carrier, porous oxides such as silica, alumina, titania, magnesia, and zirconia are used; silica or alumina is preferable, and silica is more preferable. Examples of the active metal include cobalt, ruthenium, iron, and nickel; cobalt and/or ruthenium is preferable, and cobalt is more preferable. The amount of the active metal to be supported is preferably 3 to 50% by mass, and more preferably 10 to 40% by mass based on the mass of the carrier. In the case where the amount of the active metal to be supported is less than 3% by mass, the activity tends to be insufficient; in the case where the amount of the active metal to be supported is more than 50% by mass, the activity tends to be reduced by aggregation of the active metal. Other than the active metal, other components may be supported in the FT synthesis catalyst in order to improve the activity or control the number of carbon atoms of hydrocarbon to be produced and distribution thereof. Examples of the other component include a compound containing a metal element such as zirconium, titanium, hafnium, sodium, lithium, and magnesium. It is preferable that the average particle size of the FT synthesis catalyst particle be 40 to 150 μm so that the catalyst particles may easily flow within the slurry bed reactor as a slurry suspended in the liquid hydrocarbon. It is also preferable that from the viewpoint of the fluidity as the slurry, the shape of the FT synthesis catalyst particle be spherical.

The active metal is supported by the carrier by a known method. Examples of the compound containing the active metal element used for supporting can include salts of mineral acid of the active metal such as nitric acid salts, hydrochloric acid salts, and sulfuric acid salts; salts of organic acid such as formic acid, acetic acid, and propionic acid; and complexes such as acetylacetonate complexes. The supporting method is not particularly limited, and an impregnation method represented by an Incipient Wetness method using a solution of a compound containing the active metal element is preferably used. The carrier by which the compound containing the active metal element is supported is dried by a known method, and more preferably fired under an air atmosphere by a known method. The firing temperature is not particularly limited, and usually approximately 300 to 600° C. By the firing, the compound containing the active metal element on the carrier is converted into metal oxide.

For the FT synthesis catalyst in order to demonstrate high activity to the FT synthesis reaction, it is necessary that the active metal atom be converted into a metal by reduction treatment of the catalyst in which the active metal atom is oxidized. The reduction treatment is usually performed by contacting the catalyst with reducing gas under heating. Examples of the reducing gas include hydrogen gas, gases containing hydrogen gas such as a mixed gas of hydrogen gas and an inert gas such as nitrogen gas, and carbon monoxide gas; preferable is hydrogen containing gas, and more preferable is hydrogen gas. The temperature in the reduction treatment is not particularly limited, and it is preferable that it be usually 200 to 550° C. At a reduction temperature less than 200° C., the active metal atom tends not to be sufficiently reduced and not to sufficiently demonstrate the catalyst activity; at a temperature more than 550° C., the catalyst activity tends to be reduced due to aggregation of the active metal or the like. The pressure in the reduction treatment is not particularly limited, and it is preferable that it be usually 0.1 to 10 MPa. At a pressure less than 0.1 MPa, the active metal atom tends not to be sufficiently reduced and not to sufficiently demonstrate the catalyst activity; at a pressure more than 10 MPa, facility cost tends to be increased for a need to increase pressure resistance of the apparatus. The time of the reduction treatment is not particularly limited, and it is preferable that it be usually 0.5 to 50 hours. At a reduction time less than 0.5 hours, the active metal atom tends not to be sufficiently reduced and not to sufficiently demonstrate the catalyst activity; at a reduction time more than 50 hours, the catalyst activity tends to be reduced due to aggregation of the active metal or the like, and the efficiency tends to be reduced. The facility in which the reduction treatment is performed is not particularly limited; for example, the reduction treatment may be performed in the absence of liquid hydrocarbon within the reactor to perform the FT synthesis reaction. The reduction treatment may also be performed within a facility connected to the reactor to perform the FT synthesis reaction, and the catalyst may be transferred through a piping to the reactor to perform the FT synthesis without contacting the catalyst with the air.

On the other hand, in the case where the reduction treatment is performed in a facility located in a place different from that of the facility to perform the FT synthesis reaction such as a catalyst production facility, the catalyst activated by the reduction treatment is deactivated if the catalyst is contacted with the air during transportation or the like. In order to prevent this deactivation, it is preferable that the activated catalyst is subjected to a stabilization treatment. Examples of the stabilization treatment include a method for performing a light oxidation treatment on an activated catalyst to form an oxidation coating on the surface of an active metal so as not to further progress oxidation due to contact with the air, or a method for coating an activated catalyst with hydrocarbon wax or the like in the absence of the air to block contact with the air. In the method for forming the oxidation coating, the catalyst can be fed to the FT synthesis reaction as it is after transportation; in the method for performing coating with wax or the like, when the catalyst is suspended in a liquid hydrocarbon to form a slurry, the wax or the like used for coating is dissolved in liquid hydrocarbon, and the activity is demonstrated.

The reaction condition on the FT synthesis reaction in the bubble column type slurry bed reactor C2 is not limited; for example, the following reaction condition is selected. Namely, it is preferable that the reaction temperature be 150 to 300° C. from the viewpoint of increase in the conversion rate of carbon monoxide and the number of carbon atoms of hydrocarbon to be produced. It is preferable that the reaction pressure be 0.5 to 5.0 MPa. It is preferable that a hydrogen/carbon monoxide ratio (molar ratio) in the raw material gas be 0.5 to 4.0. It is desirable that the conversion rate of carbon monoxide be not less than 50% from the viewpoint of the production efficiency of the FT synthetic oil.

Inside of the bubble column type slurry bed reactor C2, a slurry in which the FT synthesis catalyst particles are suspended in the liquid hydrocarbon (preferably the product of the FT synthesis reaction) is accommodated. The synthesis gas (CO and $H_2$) obtained in Step S1 is injected into the slurry within the reactor through a dispersion plate installed in the bottom of the bubble column type slurry bed reactor C2. The synthesis gas blown into the slurry becomes bubbles, which move upward in the slurry to the upper portion of the bubble column type slurry bed reactor C2. In the course thereof, the synthesis gas is dissolved in the liquid hydrocarbon to contact the FT synthesis catalyst particles; thereby, the FT synthesis reaction progresses to produce hydrocarbon. The FT synthesis reaction is represented by reaction equation (3) below, for example.

$$2nH_2 + nCO \longrightarrow (-CH_2-)_n + nH_2O \tag{3}$$

A gaseous phase exists in the upper portion of the slurry accommodated in the bubble column type slurry bed reactor C2. The light hydrocarbon that is produced by the FT synthesis reaction and gaseous under the condition within the bubble column type slurry bed reactor C2 and the non-reacted synthesis gas (CO and $H_2$) move from the slurry phase to the gaseous phase portion, and are further evacuated from the top of the bubble column type slurry bed reactor C2 through the line L2. Then, by the gas liquid separator D2 including a cooler (not shown) and connected to the line L2, the evacuated light hydrocarbon and the non-reacted synthesis gas are separated into the gas content containing the non-reacted synthesis gas and hydrocarbon gas having $C_4$ or less as principal components and a liquid hydrocarbon (light hydrocarbon oil) liquefied by cooling. Of these, the gas content is recycled to the bubble column type slurry bed reactor C2, and the non-reacted synthesis gas contained in the gas content is fed to the FT synthesis reaction again. On the other hand, the light hydrocarbon oil is fed through a line L4 and a line L8 to the first rectifying column C4.

On the other hand, the hydrocarbon (heavy hydrocarbon oil) that is produced by the FT synthesis reaction and a liquid under the condition within the bubble column type slurry bed reactor C2 and the slurry containing the FT synthesis catalyst particles are fed from the central portion of the bubble column type slurry bed reactor C2 through the line L6 to the catalyst separator D4. The FT synthesis catalyst particles in the slurry are captured by the filter installed within the catalyst separator D4. The heavy hydrocarbon oil in the slurry passes through the filter to be separated from the FT synthesis catalyst particles, and is evacuated from the line L8 to merge with the light hydrocarbon oil from the line L4. The mixture of the heavy hydrocarbon oil and the light hydrocarbon oil is heated in a heat exchanger H2 installed halfway of the line L8, and then fed to the first rectifying column C4.

As the product of the FT synthesis reaction, the hydrocarbon (light hydrocarbon) that is gaseous under the condition within the bubble column type reactor C2 and the hydrocarbon (heavy hydrocarbon oil) that is a liquid under the condition within the bubble column type reactor C2 are obtained. These hydrocarbons are substantially normal paraffin, and few aromatic hydrocarbon, naphthene hydrocarbon and iso-paraffin are contained. Distribution of the number of carbon atoms of the light hydrocarbon and heavy hydrocarbon oil in total widely ranges from $C_4$ or less as a gas at normal temperature to approximately $C_{80}$, for example, as a solid (wax) at room temperature. The reaction product also contains olefins and oxygen-containing compounds containing oxygen atoms derived from carbon monoxide (e.g., alcohols) as a by-product.

If the opening of the filter that the catalyst separator D4 includes is smaller than the particle size of the FT synthesis catalyst particle, the size of the opening is not particularly limited, preferably 10 to 20 μm, and more preferably 10 to 15 μm. The FT synthesis catalyst particles captured by the filter that the catalyst separator D4 includes are re-introduced through the line L10 into the bubble column type reactor C2 by properly flowing (backwashing) the liquid hydrocarbon in a direction opposite to the ordinary flow direction, and re-used.

Part of the FT synthesis catalyst particles that flow as the slurry in the bubble column type slurry bed reactor C2 wear or collapse due to friction between the catalyst particles, friction with the wall of the apparatus or the heat conducting pipe provided within the reactor for cooling, or damages or the like caused by the reaction heat to produce the catalyst fine powder. Here, the particle size of the catalyst fine powder is not particularly limited, and is a size such that the catalyst fine powder may pass through the filter that the catalyst separator D4 includes, namely, the particle size is equal to or smaller than the size of the opening of the filter. For example, in the case where the opening of the filter is 10 μm, a catalyst particle having a particle size of not more than 10 μm is referred to as the catalyst fine powder. The catalyst fine powder contained in the slurry passes through the filter with the heavy hydrocarbon oil, and fed to the first rectifying column C4.

(Step S3)

In Step S3, the hydrocarbon oil comprising the mixture of the light hydrocarbon oil and heavy hydrocarbon oil fed from the bubble column type slurry bed reactor C2 (FT synthetic oil) is fractionated in the first rectifying column C4. By the fractionation, the FT synthetic oil is separated into the crude naphtha fraction having approximately $C_5$ to $C_{10}$ whose boiling point is lower than approximately 150° C., the crude intermediate fraction having approximately $C_{11}$ to $C_{20}$ whose boiling point is approximately 150 to 360° C., and the crude wax fraction having approximately $C_{21}$ or more whose boiling point is approximately more than 360° C.

The crude naphtha fraction is evacuated through a line L20 connected to the column top of the first rectifying column C4. The crude intermediate fraction is evacuated through a line L18 connected to the central portion of a first rectifying column C4. The crude wax fraction is evacuated through the line L12 connected to the bottom of the first rectifying column C4.

The catalyst fine powder contained in the FT synthetic oil to be fed to the first rectifying column C4 does not accompany the distilled oil obtained by vaporization once and subsequent condensation within the first rectifying column C4 (crude naphtha fraction and crude intermediate fraction), and substantially accompanies only the crude wax fraction that is not vaporized within the first rectifying column C4 but kept in a liquid state to become the column bottom oil. Accordingly, the catalyst fine powder contained in the FT synthetic oil (the whole fractions) is to be condensed in the crude wax fraction. Thereby, specifically, in the step of capturing and removing the catalyst fine powder described later, as the concentration of the catalyst fine powder in the target crude wax fraction is increased, the amount of the liquid to be treated is reduced; accordingly, capturing and removal of the catalyst fine powder can be efficiently performed.

(Step S4)

In Step S4, at least part of the crude wax fraction separated in Step S3 is transferred from the column bottom of the first rectifying column C4 through the line L12 and the transfer line L14a to the storage tank T2; in the storage tank T2, the catalyst fine powder contained in the crude wax fraction is sedimented to the bottom of the storage tank T2 and separated from the crude wax fraction to be captured.

The line L12 connected to the column bottom of the first rectifying column C4 is connected to the mixing drum D6, and the mixing drum D6 and the hydrocracker C6 are connected to each other through the line L16. The line L12 and line L16 through the mixing drum D6 form the bypass line. Here, the bypass line means a line connecting the column bottom of the first rectifying column C4 to the hydrocracker C6 without passing through the storage tank T2 for capturing and removing the catalyst fine powder from the crude wax fraction. The transfer line L14a is branched from the branching point on the line L12, and connected to the storage tank T2. The transfer line L14b for discharging the supernatant of the crude wax fraction, from which the catalyst fine powder is removed, from the storage tank T2 is connected to the line L12 downstream of the branching point. As described above, it may be configured so that the production system 100 has no transfer line L14b, and discharges the supernatant of the crude wax fraction from the storage tank T2 using the transfer line L14a. It is preferable that the line L12 (preferably, the position downstream of the branching point of the transfer line L14a and upstream of a merging point of the transfer line L14b) that form the bypass line, the transfer line L14a, and the transfer line L14b each be provided with a flow meter and a valve for closing/opening the line and adjusting the flow rate.

In the example above, it is configured that the transfer line L14a is branched from the line L12; it may be configured that the transfer line L14a is branched from the line L16, and the transfer line L14b returns to the line L16. In this case, however, because the catalyst fine powder contained in the crude wax fraction is diluted by the column bottom oil (uncracked wax fraction) of the second rectifying column C12 recycled through the line L38, an effect of condensing the catalyst fine powder in Step S3 is reduced; accordingly, it is preferable that the transfer line L14a be branched from the line L12, and returns to the line L12 as described above.

The storage tank T2 may be an ordinary storage tank (tank), and may serve as a storage tank for temporarily storing the crude wax fraction in order to balance the outflow rate of the crude wax fraction separated in Step S3 and the feeding rate of the crude wax fraction to the hydrocracker C6.

It is preferable that the bottom of the storage tank T2 include a structure for suppressing movement of the catalyst fine powder sedimented to the bottom thereof. The structure for suppressing movement of the catalyst fine powder sedimented to the bottom is one in which the movement or flow of the catalyst fine powder sedimented to the bottom and/or the crude wax fraction in the vicinity thereof is inhibited geometrically or by other mechanism, thereby to sediment the catalyst fine powder once to the bottom of the storage tank T2 and suppress movement (float) of the captured catalyst fine powder. Examples of such a structure include a structure having a bottom plate or a depression and a projection or a depression on the bottom plate in which the catalyst fine powder is captured by the depression; a structure having a partition plate on a bottom plate in which the catalyst fine powder is captured in each segment defined by the partition plates; a structure having a three-dimensional mesh pattern structure on a bottom plate in which the catalyst fine powder is captured in a space formed by the pattern; a structure having a plate-like body installed above the bottom plate spaced from the bottom plate at a predetermined interval approximately parallel thereto and having an opening, in which the catalyst fine powder passing through the opening is captured on the bottom plate; and a structure in which a magnetic material is arranged in the bottom plate, and magnetic catalyst fine powder is captured.

Figure 2:
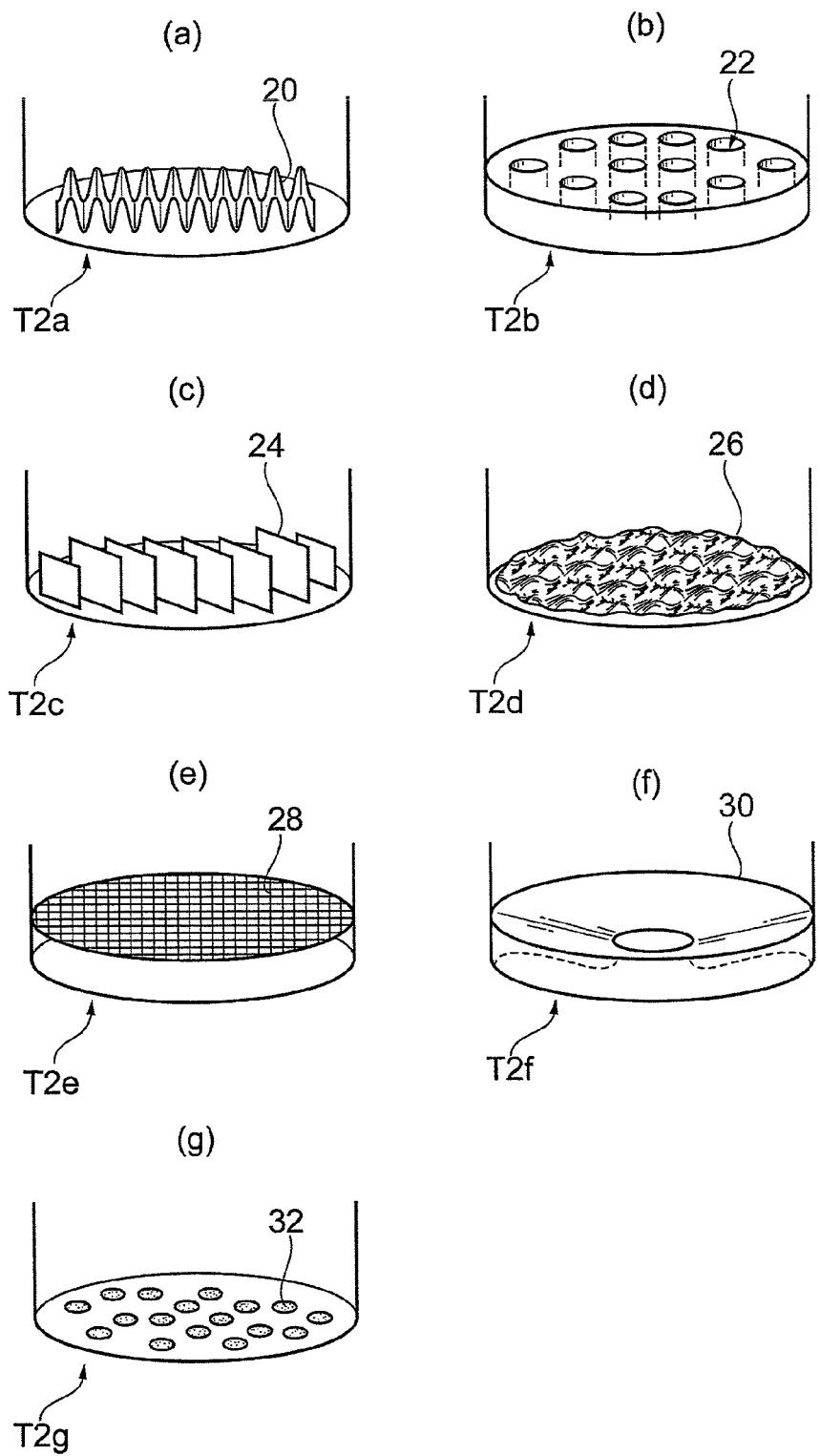
FIGS. 2(A), 2(B), 2(C), 2(D), 2(E), 2(F), and 2(G) each are a schematic view showing a specific example of a structure in the bottom of a storage tank that the system for producing a hydrocarbon oil according to the embodiment of the present invention includes.
Figure 3:
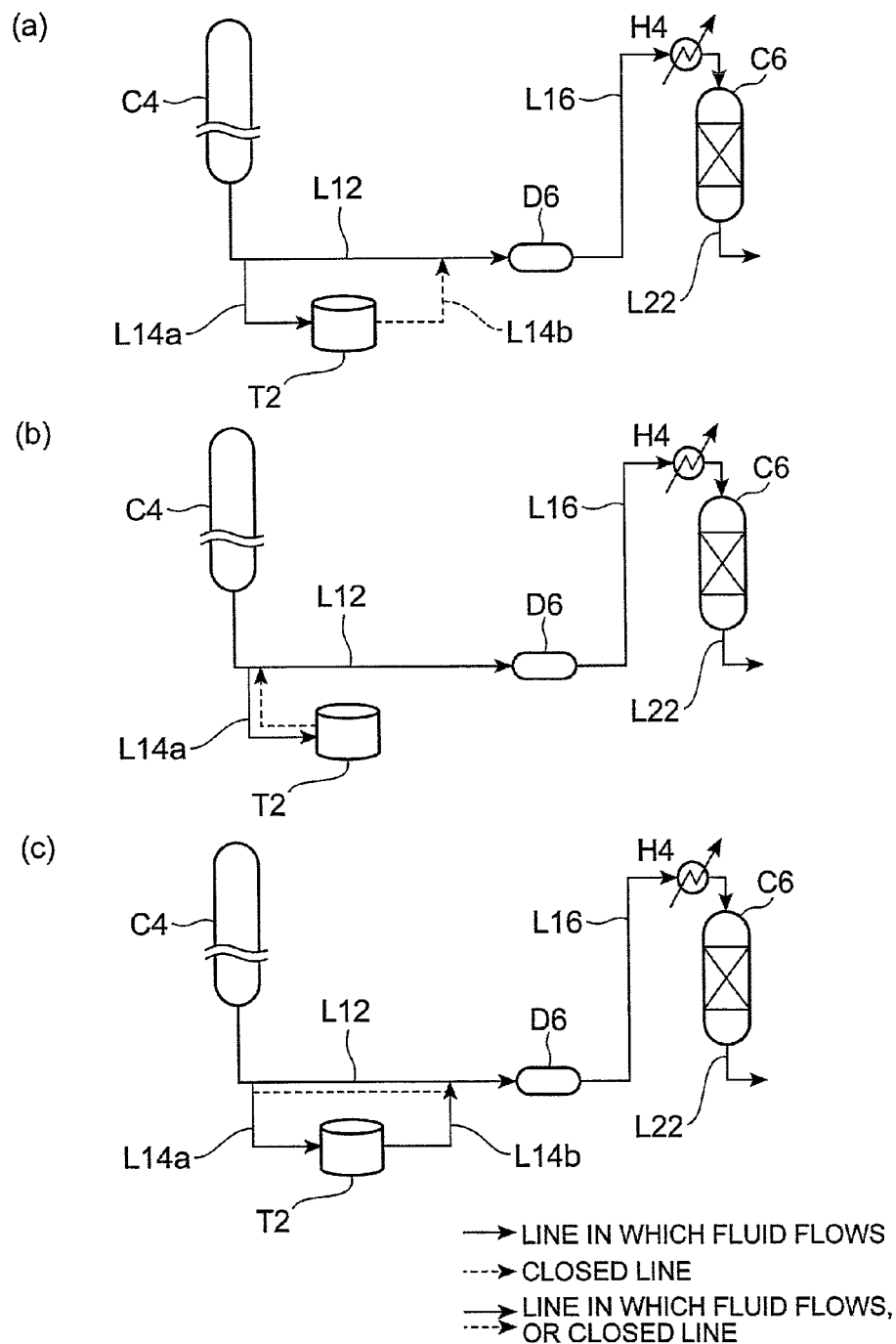
FIGS. 3(A), 3(B), and 3(C) each are a schematic view showing a specific example of an arrangement of a storage tank that the system for a hydrocarbon oil according to the embodiment of the present invention includes.

Hereinafter, each of the structures of the bottom of the storage tank T2 will be described more specifically with reference to FIG. 2.

<Structure Having Depression and Projection or Depression>

Examples of the structure having a bottom plate or a depression and a projection or a depression on the bottom plate in which the catalyst fine powder is captured by the depression include a structure having a corrugated plate shown in FIG. 2(A). FIG. 2(A) shows an example in which a corrugated plate 20 is installed on a flat bottom plate; the bottom plate of the storage tank T2 itself may have such a structure. The corrugated plate may cover the entire surface of the bottom plate. The width (pitch) of repeating units, height of the corrugated shape and the like of the corrugated plate are properly determined. The sedimented catalyst fine powder is captured by the depression of the corrugated plate. Other examples of the structure having a bottom plate or a depression and a projection or a depression on the bottom plate in which the catalyst fine powder is captured by the depression include a structure having a depression 22 as shown in FIG. 2(B). FIG. 2(B) shows an example in which the shape of the depression is cylindrical, but the shape is not limited to this, and may be other shape, e.g., prismatic, semi-spherical, or the like. The size and depth of each depression, the number of the depressions, and the like are properly determined.

<Structure Having Partition Plate>

Examples of the structure having a partition plate on the bottom plate in which the catalyst fine powder is captured in each segment defined by the partition plates include a structure as shown in FIG. 2(C). It is preferable that a partition plate 24 be provided vertical to the bottom plate, but not limited to this. In FIG. 2(C), the partition plates are provided parallel to each other on the bottom plate, but not limited to this arrangement; examples thereof include an arrangement having a lattice partition plate in a plan view that is a combination of the partition plates parallel to each other shown in FIG. 2(C) with partition plates intersecting perpendicular thereto; an arrangement having partition plates concentrically provided in a plan view; an arrangement having partition plates spirally provided in a plan view; an arrangement having partition plates provided radially from the center in a plan view; or an arrangement having partition plates in combination thereof. Here, the height, interval, and the like of each partition plate are arbitrarily determined.

<Structure Having Three-Dimensional Mesh Structure>

Examples of the structure having a three-dimensional mesh pattern structure on the bottom plate in which the catalyst fine powder is captured in a space formed by the pattern include a structure in which an entangled fibrous structure 26 is installed on the bottom plate, as shown in FIG. 2(D). The material that forms the structure may be those comprising a metal fiber such as entangled iron fibers (steel wire), woven fabrics and non-woven fabrics formed from a synthetic fiber having heat resistance, or the like, for example. In these structures, spaces are formed between the entangled fibers, and the sedimented catalyst fine powder is captured by the spaces, for example.

<Structure Having Plate-Like Body Having Opening Above Bottom Plate>

Examples of structure having a plate-like body installed above the bottom plate spaced from the bottom plate at a predetermined interval approximately parallel thereto and having an opening, in which the catalyst fine powder passing through the opening is captured on the bottom plate include a structure having a mesh 28 above the bottom plate as shown in FIG. 2(E). The opening of the mesh is not particularly limited as long as the catalyst fine powder can pass through the opening, and is determined depending on the balance between possibility in sediment of the catalyst fine powder and an effect of suppressing the catalyst fine powder once sedimented to the bottom plate passing through the mesh again to float above the mesh. Other examples of the structure having a plate-like body installed above the bottom plate spaced from the bottom plate at a predetermined interval approximately parallel thereto and having an opening, in which the catalyst fine powder passing through the opening is captured on the bottom plate include a structure having a plate-like body 30 above the bottom plate, the plate-like body 30 having a funnel-shaped structure having an inclination from the periphery toward the center and an opening in the center as shown in FIG. 2(F). FIG. 2(F) shows an example in which the plate-like body having one funnel-shaped structure covers the cross section of the storage tank T2 in the horizontal direction, while the number of the funnel-shaped structure may be plural. In that case, it is preferable that the area in the horizontal portion between the funnel-shaped structures be made as small as possible. The shape of the funnel-shaped structure not only is conical, but also may be a polygonal pyramid such as a quadrangular pyramid. The number of these funnel-shaped structures, an inclination of the inclined portion, the size of the opening, and the like are properly determined.

The structures of the bottom of the storage tank T2 above are those in which the flow of the catalyst fine powder captured by sediment due to convection of the crude wax in the vicinity thereof is geometrically inhibited, or movement of the captured catalyst fine powder out of the segments geometrically partitioned is inhibited even if the flow occurs, thereby to suppress discharging of the catalyst fine powder from the storage tank T2 by "floating."

<Structure in which Magnetic Material is Arranged in Bottom Plate>

Examples of the structure in which a magnetic material is provided in the bottom plate, and magnetic catalyst fine powder is captured include a structure in which a magnetic body 32 such as a permanent magnet is provided in the bottom plate, for example, as shown in FIG. 2(G). As the FT synthesis catalyst, a catalyst in which a magnetic metal such as cobalt, iron, and nickel as an active metal is supported by a carrier such as silica is usually used. Accordingly, when the catalyst fine powder derived from the FT synthesis catalyst and having these metals is sedimented to the bottom of the storage tank T2, the catalyst fine powder is adsorbed by a magnetic force of the magnetic body provided in the bottom; then, movement thereof is suppressed even if the flow occurs in the crude wax fraction in the vicinity thereof. The magnetic material may be an electromagnet other than the permanent magnet; in that case, a single or a plurality of electromagnets are provided in the bottom of the storage tank T2, and an electric facility for generating magnetism in the electromagnet is installed; the electric facility is electrically conducted when the catalyst fine powder is captured in the storage tank T2.

The structure for suppressing movement of the catalyst fine powder sedimented to the bottom of the storage tank T2 is not limited to the examples above, and any structure that can suppress the movement or flow of the catalyst fine powder sedimented to the bottom of the storage tank T2 and/or the crude wax fraction in the vicinity thereof by the same or similar action and effect as or to those above can be used.

The transfer line L14a, the transfer line L14b, and the storage tank T2 may be composed of the corresponding individual lines and an individual storage tank provided therebetween, or composed of a plurality of lines and storage tanks in which the transfer line L14a and the transfer line L14b each are branched into a plurality of lines parallel to each other, and each of the storage tanks is provided between these branched lines.

The capturing of the catalyst fine powder contained in the crude wax fraction in the storage tank T2 comprises: a transferring step of transferring at least part of the crude wax fraction flowed from the column bottom of the first rectifying column C4 to the storage tank T2, and a discharging step of discharging the supernatant obtained by sedimenting the catalyst fine powder in the crude wax fraction transferred to the storage tank T2 from the storage tank T2; the transferring step and the discharging step may be performed at the same time. Alternatively, the discharging step may be performed after end of the transferring step. Further, a settling step of settling the crude wax fraction without performing transfer and discharge may be provided between the transferring step and the discharging step. In order to securely capture the catalyst fine powder in the crude wax fraction, it is preferable that capturing of the catalyst fine powder comprise the transferring step, the settling step, and the discharging step in this order. A specific method for operation of these will be described later.

(Step S5)

In Step S5, of the crude wax fraction that is the column bottom of the first rectifying column oil C4 separated in Step S3 and contains the catalyst fine powder, the remaining crude wax fraction not transferred to the storage tank T2 in Step S4 is transferred through the line L12 and line L16 that form the bypass line from the first rectifying column C4 to the hydrocracker C6, and/or the supernatant of the crude wax fraction in which the catalyst fine powder is captured by sediment at the bottom in the storage tank T2 is transferred through the transfer line L14b (transfer line L14a and line L12 in some cases) and the line L16 from the storage tank T2 to the hydrocracker C6.

Next, a specific method will be described in which in Step S4 and Step S5, at least part of the crude wax fraction flowed from the column bottom of the first rectifying column C4 is transferred to the storage tank T2 to capture the catalyst fine powder, and the supernatant of the crude wax fraction in which the catalyst fine powder is captured and/or the remaining crude wax fraction not transferred to the storage tank T2 is transferred to the hydrocracker C6. It is preferable that hydrocracking of the crude wax fraction in the hydrocracker C6 (Step S6) be continuously performed; for that, in Step S5, transfer of the crude wax fraction through the bypass line and/or the transfer line L14b (transfer line L14a and line L12 in some cases) and the line L16 from the storage tank T2 to the hydrocracker C6 needs to be continuously performed.

In the case where the storage tank T2 is composed of a single storage tank, at least part of the crude wax fraction flowed from the column bottom of the first rectifying column may be transferred through the line L12 and the transfer line L14a to the storage tank T2 (discharging from the storage tank T2 is not performed at the same time.), and at the same time, the remaining crude wax fraction may be transferred through the bypass line (line L12 and line L16) directly to the hydrocracker C6. In this case, after the crude wax fraction is transferred to the storage tank T2 or after settling is further performed, the supernatant from which the catalyst fine powder is captured is discharged from the storage tank T2, and transferred through the transfer line L14b and the line L16 to the hydrocracker C6 (see FIG. 3(A)). In the case where the system 100 for producing a hydrocarbon oil has no transfer line L14b and has only the transfer line L14a, the supernatant is discharged using the transfer line L14a instead of the transfer line L14b, and further transferred to the hydrocracker C6 through the line L12 and the line L16 (see FIG. 3(B)).

Alternatively, at least part of the crude wax fraction flowed from the column bottom of the first rectifying column C4 may be transferred through the line L12 and the transfer line L14a to the storage tank T2, and at the same time, the supernatant from which the catalyst fine powder is captured may be discharged from the storage tank T2 through the line L14b, and further fed through the line L16 to the hydrocracker C6 (see FIG. 3(C)). At this time, in the case where of the crude wax fraction flowed from the column bottom of the first rectifying column C4, the remaining crude wax fraction not transferred to the storage tank T2 exists, the remaining crude wax fraction is fed through the bypass line (line L12 and line L16) to the hydrocracker C6.

In the case where the storage tank T2 is composed of two storage tanks (first storage tank and second storage tank) provided in parallel, the two storage tanks may be used by switching as below, for example. Namely, the crude wax fraction is transferred from the column bottom of the first rectifying column C4 to the first storage tank to be stored (discharging from the first storage tank is not performed at the same time.). After transfer of the crude wax fraction to the first storage tank is completed, the supernatant of the crude wax fraction from which the catalyst fine powder is captured is discharged from the first storage tank, and transferred through the transfer line L14b and the line L16 to the hydrocracker C6; at the same time, the crude wax fraction is transferred from the column bottom of the first rectifying column C4 to the second storage tank to be stored (discharging from the second storage tank is not performed at the same time.). After transfer of the crude wax fraction to the second storage tank is completed, the supernatant of the crude wax fraction from which the catalyst fine powder is captured is discharged from the second storage tank, and transferred through the transfer line L14b and the line L16 to the hydrocracker C6; at the same time, this time, the crude wax fraction is transferred from the column bottom of the first rectifying column C4 to the first storage tank to be stored. Hereinafter, in the same manner, the two storage tanks are switched, and transfer, storage, and discharge are alternately repeated; thereby, the supernatant of the crude wax fraction from which the catalyst fine powder is captured can be continuously fed to the hydrocracker C6 (see FIG. 4(A)). At this time, in the case where of the crude wax fraction flowed from the column bottom of the first rectifying column C4, the remaining crude wax fraction not transferred to the storage tank T2 exists, the remaining crude wax fraction is fed through the bypass line (line L12 and line L16) to the hydrocracker C6.

In the case where the storage tank T2 is composed of three storage tanks (first storage tank, second storage tank, and third storage tank) provided in parallel, the three storage tanks may be used by switching as below, for example. Namely, the crude wax fraction is transferred to the first storage tank (transferring step); in the second storage tank, the crude wax fraction already transferred is settled and the catalyst fine powder is sedimented (settling step); in the third storage tank, the supernatant of the crude wax fraction in which sediment and capturing of the catalyst fine powder by settling are completed is discharged, and transferred to the hydrocracker C6 (discharging step). Next, in the first storage tank in which transfer of the crude wax fraction is completed, the crude wax fraction is settled and the catalyst fine powder is sedimented (settling step); in the second storage tank in which sediment and capturing of the catalyst fine powder by settling is completed, the supernatant of the crude wax fraction is discharged, and transferred to the hydrocracker C6 (discharging step); the crude wax fraction is transferred from the column bottom of the first rectifying column C4 to the third storage tank in which discharge of the supernatant is completed (transferring step). Hereinafter, in the same manner, the three storage tanks are sequentially switched, the transferring step, the settling step, and the discharging step are repeated in the respective storage tanks; thereby, the crude wax fraction from which the catalyst fine powder is removed can be continuously fed to the hydrocracker C6 (see FIG. 4(B)). At this time, in the case where of the crude wax fraction flowed from the column bottom of the first rectifying column C4, the remaining crude wax fraction not transferred to the storage tank T2 exists, the remaining crude wax fraction is fed through the bypass line (line L12 and line L16) to the hydrocracker C6.

As described above, in the system 100 for producing a hydrocarbon oil according to the present invention, examples of the embodiment in which the storage tank T2 is composed of a single storage tank, two storage tanks provided in parallel, or three storage tanks provided in parallel, and examples of a preferable embodiment of Step S4 and Step S5 in the method for producing a hydrocarbon oil according to the present invention in the respective cases have been described, but the embodiment will not be limited to these examples. For example, the storage tank T2 may be composed of four or more storage tanks provided in parallel, a plurality of storage tanks arrange in serial, or three or more storage tanks in parallel and in serial. Moreover, the embodiment of Step S4 and Step S5 in the method for producing a hydrocarbon oil according to the present invention is not particularly limited as long as the crude wax fraction flowed from the column bottom of the first rectifying column C4 is continuously fed through the bypass line and/or the discharging line from the storage tank T2 to the hydrocracker C6, and the catalyst fine powder is captured in the storage tank T2.

(Step S6)

In Step S6, the supernatant of the crude wax fraction transferred from the storage tank T2 through the transfer line L14b (transfer line L14a and line L12 in some cases) and the line L16 to the hydrocracker C6, from which the catalyst fine powder is captured in the storage tank T2 in Step S5, and/or the crude wax fraction transferred from the column bottom of the first rectifying column C4 through the bypass line (lines L12 and L16) to the hydrocracker C6, from which the catalyst fine powder is not removed, is hydrocracked in the hydrocracker C6. The crude wax fraction transferred by Step S5, with hydrogen gas fed by a feed line of the hydrogen gas connected to the line L16 (not shown), is heated to a temperature needed for hydrocracking of the crude wax fraction by a heat exchanger H4 provided in the line L16, and then fed to the hydrocracker C6 to be hydrocracked. The crude wax fraction not sufficiently hydrocracked in the hydrocracker C6 (hereinafter, referred to as the "uncracked wax fraction" in some cases) is recovered as the column bottom oil of the second rectifying column C12 in Step S9, recycled by a line L38 to the line L12, mixed with the crude wax fraction from the first rectifying column C4 and/or the storage tank T2 in the mixing drum D6, and fed to the hydrocracker C6 again.

The type of the hydrocracker C6 is not particularly limited, and a fixed bed flow reactor filled with a hydrocracking catalyst is preferably used. The reactor may be singular, or a plurality of reactors may be provided in serial or in parallel. Moreover, the catalyst bed within the reactor may be singular or plural.

As the hydrocracking catalyst filled in the hydrocracker C6, a known hydrocracking catalyst is used, and a catalyst in which a metal that has hydrogenation activity and belongs to Group 8 to Group 10 in the periodic table of the elements is supported by an inorganic carrier having a solid acidity is preferably used.

Examples of the inorganic carrier that forms the hydrocracking catalyst and has suitable solid acidity include those comprising crystalline zeolite such as ultra stable Y-type (USY) zeolite, Y-type zeolite, mordenite, and β zeolite, and one or more inorganic compounds selected from amorphous composite metal oxides having heat resistance such as silica alumina, silica zirconia, and alumina boria. Further, as the carrier, compositions comprising USY zeolite and one or more amorphous composite metal oxides selected from silica alumina, alumina boria, and silica zirconia are more preferable, and compositions comprising USY zeolite and alumina boria and/or silica alumina are still more preferable.

USY zeolite is the one obtained by ultra-stabilizing Y-type zeolite by a hydrothermal treatment and/or acid treatment; in addition to the micro fine porous structure called micro fine pores that Y-type zeolite originally has and whose pore size is not more than 2 nm, new fine pores having a pore size in the range of 2 to 10 nm are formed in USY zeolite. The average particle size of USY zeolite is not particularly limited, preferably not more than 1.0 μm, and more preferably not more than 0.5 μm. Moreover, in USY zeolite, it is preferable that the molar ratio of silica/alumina (molar ratio of silica to alumina) be 10 to 200, and it is more preferable that the molar ratio be 15 to 100, and it is still more preferable that the molar ratio be 20 to 60.

Moreover, it is preferable that the carrier contain 0.1 to 80% by mass of crystalline zeolite and 0.1 to 60% by mass of amorphous composite metal oxide having heat resistance.

The carrier can be produced as follows: a carrier composition comprising the inorganic compound having solid acidity and a binder is molded, and fired. The proportion of the inorganic compound having solid acidity to be blended is preferably 1 to 70% by mass, and more preferably 2 to 60% by mass based on the whole mass of the carrier. Moreover, in the case where the carrier contains USY zeolite, the proportion of USY zeolite to be blended is preferably 0.1 to 10% by mass, and more preferably 0.5 to 5% by mass based on the whole mass of the carrier. Further, in the case where the carrier contains USY zeolite and alumina boria, it is preferable that the proportion of USY zeolite to alumina boria to be blended (USY zeolite/alumina boria) be 0.03 to 1 in the mass ratio. Moreover, in the case where the carrier contains USY zeolite and silica alumina, it is preferable that the proportion of USY zeolite to silica alumina to be blended (USY zeolite/silica alumina) be 0.03 to 1 in the mass ratio.

The binder is not particularly limited; alumina, silica, titania, magnesia are preferable, and alumina is more preferable. The amount of the binder to be blended is preferably 20 to 98% by mass, and more preferably 30 to 96% by mass based on the whole mass of the carrier.

The temperature in firing the carrier composition is preferably in the range of 400 to 550° C., more preferably in the range of 470 to 530° C., and still more preferably in the range of 490 to 530° C. Firing at such a temperature can give sufficient solid acidity and mechanical strength to the carrier.

Examples of Group 8 to Group 10 metals in the periodic table supported by the carrier and having hydrogenation activity specifically include cobalt, nickel, rhodium, palladium, iridium, and platinum. Among these, metals selected from nickel, palladium, and platinum are preferably used singly or in combinations of two or more. These metals can be supported on the carrier mentioned above by a standard method such as impregnation and ion exchange. The amount of the metal to be supported is not particularly limited, and it is preferable that the total amount of the metal be 0.1 to 3.0% by mass based on the mass of the carrier. Here, the periodic table of the elements refers to the long form of the periodic table of the elements based on the specification by IUPAC (the International Union of Pure and Applied Chemistry).

In the hydrocracker C6, the crude wax fraction and part of the uncracked wax fraction (hydrocarbons having approximately $C_{21}$ or more) are converted into hydrocarbons having approximately $C_{20}$ or less by hydrocracking; further, part thereof is converted into naphtha fraction (approximately $C_5$ to $C_{10}$) lighter than the target intermediate fraction (approximately $C_{11}$ to $C_{20}$) and further gaseous hydrocarbons having $C_4$ or less by excessive cracking. On the other hand, the crude wax fraction and part of the uncracked wax fraction are not subjected to sufficiently hydrocracking, and become the uncracked wax fraction having approximately $C_{21}$ or more. The composition of the hydrocracking product is determined according to the hydrocracking catalyst to be used and the hydrocracking reaction condition. Here, the "hydrocracking product" refers to all hydrocracking products containing the uncracked wax fraction, unless otherwise specified. If the hydrocracking reaction condition is tighter than necessary, the content of the uncracked wax fraction in the hydrocracking product is reduced while the light content which weight is equal to or lighter than the naphtha fraction is increased to reduce yield of the target intermediate fraction. On the other hand, if the hydrocracking reaction condition is milder than necessary, the uncracked wax fraction is increased to reduce yield of the intermediate fraction. In the case where the ratio of the cracking product whose boiling point is 25 to 360° C. to the whole cracking products whose boiling point is not less than 25° C. ([mass of the cracking product whose boiling point is 25 to 360° C./mass of the whole cracking products whose boiling point is not less than 25° C.]×100(%)) is defined as a "cracking rate," the reaction condition is selected so that the cracking rate may be usually 20 to 90%, preferably 30 to 80%, more preferably 45 to 70%.

In the hydrocracker C6, in parallel with the hydrocracking reaction, a hydrogenation isomerization reaction of normal paraffin that includes the crude wax fraction and uncracked wax fraction or hydrocracking products thereof progresses to produce isoparaffin. In the case where the hydrocracking product is used as the fuel oil base material, isoparaffin to be produced by the hydrogenation isomerization reaction is a component that makes contribution to improvement in fluidity at a low temperature, and it is preferable that the production rate be high. Further, removal of olefins and oxygen-containing compounds such as alcohols that are by-products of the FT synthesis reaction contained in the crude wax fraction also progresses. Namely, olefins are converted into paraffin hydrocarbons by hydrogenation, and the oxygen-containing compounds are converted into paraffin hydrocarbon and water by hydrodeoxidation.

The reaction condition in the hydrocracker C6 is not limited, and the following reaction condition can be selected. Namely, examples of the reaction temperature include 180 to 400° C.; 200 to 370° C. is preferable, 250 to 350° C. is more preferable, and 280 to 350° C. is particularly preferable. At a reaction temperature more than 400° C., not only does cracking into the light content tend to progress to reduce the yield of the intermediate fraction, but the product tends to be colored to limit use as the fuel oil base material. On the other hand, at a reaction temperature less than 180° C., not only does the hydrocracking reaction tend not to sufficiently progress to reduce the yield of the intermediate fraction, but production of isoparaffin by the hydrogenation isomerization reaction tends to be suppressed, and the oxygen-containing compounds such as alcohols tend not to be sufficiently removed to remain. Examples of the hydrogen partial pressure include 0.5 to 12 MPa, and 1.0 to 5.0 MPa is preferable. At a hydrogen partial pressure less than 0.5 MPa, hydrocracking, hydrogenation isomerization and the like tend not to sufficiently progress; on the other hand, at a hydrogen partial pressure more than 12 MPa, high pressure resistance is demanded of the apparatus, and facility cost tends to be increased. Examples of the liquid hourly space velocity (LHSV) of the crude wax fraction and uncracked wax fraction include 0.1 to 10.0 $h^{-1}$, and 0.3 to 3.5 $h^{-1}$ is preferable. At an LHSV less than 0.1 $h^{-1}$, hydrocracking tends to excessively progress, and productivity tends to be reduced; on the other hand, at an LHSV more than 10.0 $h^{-1}$, hydrocracking, hydrogenation isomerization and the like tend not to sufficiently progress. Examples of the ratio of hydrogen/oil include 50 to 1000 NL/L, and 70 to 800 NL/L is preferable. At a ratio of hydrogen/oil less than 50 NL/L, hydrocracking, hydrogenation isomerization and the like tend not to sufficiently progress; on the other hand, at a ratio of hydrogen/oil more than 1000 NL/L, a large-sized hydrogen feeding apparatus or the like tends to be needed.

In this example, the hydrocracking product and non-reacted hydrogen gas flowed from the hydrocracker C6 are cooled, and separated into gas and liquid at two stages by a gas liquid separator D8 and a gas liquid separator D10, the relatively heavy liquid hydrocarbon containing the uncracked wax fraction is obtained from the gas liquid separator D8, and the gas content mainly containing hydrogen gas and gaseous hydrocarbons having $C_4$ or less and the relatively light liquid hydrocarbon are obtained from the gas liquid separator D10. By such two-stage cooling and gas liquid separation, the occurrence of clogging of the line accompanied by solidification by rapid cooling of the uncracked wax fraction contained in the hydrocracking product, or the like can be prevented. The liquid hydrocarbons each obtained in the gas liquid separator D8 and the gas liquid separator D10 merge with a line L32 through a line L28 and a line L26, respectively. The gas content separated in a gas liquid separator D12 and mainly containing hydrogen gas and gaseous hydrocarbon having $C_4$ or less is fed to the intermediate fraction hydrorefining apparatus C8 and the naphtha fraction hydrorefining apparatus C10 through a line (not shown) connecting the gas liquid separator D10 to the line L18 and the line L20, and hydrogen gas is re-used.

(Step S7)

In Step S7, the crude intermediate fraction evacuated from the first rectifying column C4 through the line L18, with the hydrogen gas fed by a feed line of the hydrogen gas connected to the line L18 (not shown), is heated to the temperature needed for hydrorefining of the crude intermediate fraction by a heat exchanger H6 provided in the line L18, and fed to the intermediate fraction hydrorefining apparatus C8 to be hydrorefined.

The type of the intermediate fraction hydrorefining apparatus C8 is not particularly limited, and a fixed bed flow reactor filled with a hydrorefining catalyst is preferably used. The reactor may be singular, or a plurality of reactors may be provided in serial or in parallel. Moreover, the catalyst bed within the reactor may be singular or plural.

As the hydrorefining catalyst used in the intermediate fraction hydrorefining apparatus C8, catalysts usually used for hydrorefining and/or hydrogenation isomerization in petroleum refining or the like, namely, the catalysts in which an active metal having hydrogenation ability is supported by an inorganic carrier can be used.

As the active metal that forms the hydrorefining catalyst, one or more metals selected from the group consisting of metals in Groups 6, 8, 9, and 10 in the periodic table of the elements are used. Specific examples of these metals include noble metals such as platinum, palladium, rhodium, ruthenium, iridium, and osmium, or cobalt, nickel, molybdenum, tungsten, and iron; preferable are platinum, palladium, nickel, cobalt, molybdenum, and tungsten, and more preferable are platinum and palladium. Moreover, two or more of these metals are also preferably used in combination; examples of a preferable combination in this case include platinum-palladium, cobalt-molybdenum, nickel-molybdenum, nickel-cobalt-molybdenum, and nickel-tungsten.

Examples of the inorganic carrier that forms the hydrorefining catalyst include metal oxides such as alumina, silica, titania, zirconia, and boria. These metal oxides may be used alone, or used as a mixture of two or more thereof, or a composite metal oxide such as silica alumina, silica zirconia, alumina zirconia, and alumina boria. From the viewpoint of efficiently progressing hydrogenation isomerization of normal paraffin at the same time of hydrorefining, it is preferable that the inorganic carrier be a composite metal oxide having solid acidity such as silica alumina, silica zirconia, alumina zirconia, and alumina boria. Moreover, a small amount of zeolite may be contained in the inorganic carrier. Further, in order to improve the moldability and mechanical strength of the carrier, a binder may be blended in the inorganic carrier. Examples of a preferable binder include alumina, silica, and magnesia.

In the case where the active metal is the noble metal mentioned above, it is preferable that the content of the active metal in the hydrorefining catalyst be approximately 0.1 to 3% by mass as the metal atom based on the mass of the carrier. Moreover, in the case where the active metal is a metal other than the noble metal, it is preferable that the content be approximately 2 to 50% by mass as metal oxide based on the mass of the carrier. In the case where the content of the active metal is less than the lower limit value, hydrorefining and hydrogenation isomerization tend not to sufficiently progress. On the other hand, in the case where the content of the active metal is more than the upper limit value, dispersion of the active metal tends to be reduced to reduce the activity of the catalyst, and cost of the catalyst is increased.

In hydrorefining of the crude intermediate fraction (normal paraffin having approximately $C_{11}$ to $C_{20}$ is a main component) in the intermediate fraction hydrorefining apparatus C8, olefins that are a by-product of the FT synthesis reaction contained in the crude intermediate fraction are hydrogenated to be converted into paraffin hydrocarbon. Moreover, the oxygen-containing compounds such as alcohols are converted into paraffin hydrocarbon and water by hydrodeoxidation. Moreover, in parallel with the hydrorefining, the hydrogenation isomerization reaction of normal paraffin that forms the crude intermediate fraction progresses to produce isoparaffin. In the case where the intermediate fraction is used as the fuel oil base material, the isoparaffin produced by the hydrogenation isomerization reaction is a component that makes contribution to improvement in fluidity at a low temperature, and it is preferable that the production rate be high.

The reaction condition in the intermediate fraction hydrorefining apparatus C8 is not limited, and the following reaction condition can be selected. Namely, examples of the reaction temperature include 180 to 400° C., 200 to 370° C. is preferable, 250 to 350° C. is more preferable, and 280 to 350° C. is particularly preferable. At a reaction temperature more than 400° C., cracking into the light content tends to progress to reduce the yield of the intermediate fraction, and the product tends to be colored to limited use as fuel oil base material. On the other hand, at a reaction temperature less than 180° C., the oxygen-containing compounds such as alcohols tend not to sufficiently be removed to remain, and production of isoparaffin by the hydrogenation isomerization reaction tends to be suppressed. Examples of the hydrogen partial pressure include 0.5 to 12 MPa, and 1.0 to 5.0 MPa is preferable. At a hydrogen partial pressure less than 0.5 MPa, hydrorefining and hydrogenation isomerization tend not to sufficiently progress; on the other hand, a hydrogen partial pressure more than 12 MPa, high pressure resistance is demanded of the apparatus, and facility cost tends to be increased. Examples of the liquid hourly space velocity (LHSV) of the crude intermediate fraction include 0.1 to 10.0 $h^{-1}$, and 0.3 to 3.5 $h^{-1}$ is preferable. At an LHSV less than 0.1 $h^{-1}$, cracking into the light content tends to progress to reduce the yield of the intermediate fraction, and productivity tends to be reduced; on the other hand, at an LHSV more than 10.0 $h^{-1}$, hydrorefining and hydrogenation isomerization tend not to sufficiently progress. Examples of the ratio of hydrogen/oil include 50 to 1000 NL/L, and 70 to 800 NL/L is preferable. At a ratio of hydrogen/oil less than 50 NL/L, hydrorefining and hydrogenation isomerization tend not to sufficiently progress; on the other hand, at a ratio of hydrogen/oil more than 1000 NL/L, a large-sized hydrogen feeding apparatus and the like tend to be needed.

After the gas content mainly containing the non-reacted hydrogen gas is separated in the gas liquid separator D12 to which a line L30 is connected, an outflow oil of the intermediate fraction hydrorefining apparatus C8 is transferred through the line L32 to merge with the liquid hydrocracking product of the wax fraction transferred by the line L26. The gas content mainly containing hydrogen gas separated by the gas liquid separator D12 is fed to the hydrocracker C6, and re-used.

(Step S8)

In Step S8, the crude naphtha fraction evacuated from the first rectifying column C4 by the line L20, with the hydrogen gas fed by a feed line of the hydrogen gas (not shown) connected to the line L20, is heated to the temperature needed for hydrorefining of the crude naphtha fraction by a heat exchanger H8 installed in the line L20, and then fed to the naphtha fraction hydrorefining apparatus C10 to be hydrorefined.

The type of a naphtha fraction hydrorefining apparatus C10 is not particularly limited, and a fixed bed flow reactor filled with a hydrorefining catalyst is preferably used. The reactor may be singular, or a plurality of reactors may be provided in serial or in parallel. Moreover, the catalyst bed within the reactor may be singular or plural.

The hydrorefining catalyst used for the naphtha fraction hydrorefining apparatus 10 may be the same hydrorefining catalyst as that used for hydrorefining of the crude intermediate fraction.

In hydrorefining of the crude naphtha fraction (normal paraffin having approximately $C_5$ to $C_{10}$ is a principal component.) in the naphtha fraction hydrorefining apparatus C10, unsaturated hydrocarbon contained in the crude naphtha fraction is converted into paraffin hydrocarbon by hydrogenation. Moreover, the oxygen-containing compounds contained in the crude naphtha fraction such as alcohols are converted into paraffin hydrocarbon and water by hydrodeoxidation. In the naphtha fraction, the hydrogenation isomerization reaction does not progress much because the number of carbon atoms is small.

The reaction condition in the naphtha fraction hydrorefining apparatus C10 is not limited, and the same reaction condition as that in the intermediate fraction hydrorefining apparatus C8 mentioned above can be selected.

The outflow oil of the naphtha fraction hydrorefining apparatus C10 is fed through a line L34 to a gas liquid separator D14; in the gas liquid separator D14, the outflow oil is separated into the gas content, in which hydrogen gas is a principal component, and liquid hydrocarbon. The separated gas content is fed to the hydrocracker C6, and hydrogen gas contained in this is re-used. On the other hand, the separated liquid hydrocarbon is transferred through the line L36 to the naphtha stabilizer C14. Moreover, part of the liquid hydrocarbon is recycled through a line L48 to the line L20 upstream of the naphtha fraction hydrorefining apparatus C10. Because the amount of heat to be produced in hydrorefining of the crude naphtha fraction (hydrogenation of olefins and hydrodeoxidation of alcohols and the like), part of the liquid hydrocarbon is recycled to the naphtha fraction hydrorefining apparatus C10, and the crude naphtha fraction is diluted; thereby, increase in the temperature in the naphtha fraction hydrorefining apparatus C10 is suppressed.

In the naphtha stabilizer C14, the liquid hydrocarbon fed from the naphtha fraction hydrorefining apparatus C10 and the second rectifying column C12 is fractionated to obtain refined naphtha with carbon atoms of $C_5$ to $C_{10}$ as a product. The refined naphtha is transferred from the column bottom of the naphtha stabilizer C14 through a line L46 to a storage tank T8, and stored. On the other hand, from a line L50 connected to the column top of the naphtha stabilizer C14, hydrocarbon gas in which hydrocarbon with the number of carbon atoms of a predetermined number or less ($C_4$ or less) is a principal component is discharged. Because the hydrocarbon gas is not a target product, the hydrocarbon gas is introduced into an external burning facility (not shown) to be burned, and then discharged into the air.

(Step S9)

In Step S9, the mixed oil comprising the liquid hydrocarbon obtained from the outflow product from the hydrocracker C6 and the liquid hydrocarbon obtained from the outflow product from the intermediate fraction hydrorefining apparatus C8 is heated by a heat exchanger H10 installed in the line L32, and fed to the second rectifying column C12 to be fractionated into hydrocarbon having approximately $C_{10}$ or less, a kerosene fraction, a light oil fraction, and a uncracked wax fraction. In the hydrocarbon having approximately $C_{10}$ or less, the boiling point is lower than approximately 150° C.; the hydrocarbon is evacuated from the column top of the second rectifying column C12 by a line L44. In the kerosene fraction, the boiling point is approximately 150 to 250° C.; the kerosene fraction is evacuated from the central portion of the second rectifying column C12 by a line L42 to be stored in a storage tank T6. In the light oil fraction, the boiling point is approximately 250 to 360° C.; the light oil fraction is evacuated from the lower portion of the second rectifying column C12 by a line L40 to be stored in a storage tank T4. In the uncracked wax fraction, the boiling point exceeds 360° C.; the uncracked wax fraction is evacuated from the column bottom of the second rectifying column C12 to be recycled by the line L38 to the line L12 upstream of the hydrocracker C6. The hydrocarbon having approximately $C_{10}$ or less evacuated from the column top of the second rectifying column C12 is fed by the line L44 and the L36 to the naphtha stabilizer, and fractionated with the liquid hydrocarbon fed from the naphtha fraction hydrorefining apparatus C10.

As above, the suitable embodiment of the method for producing a hydrocarbon oil and a production system according to the present invention has been described, but the present invention will not be always limited to the embodiment described above.

For example, in the embodiment, as the GTL process, natural gas is used as the raw material for production of the synthesis gas, while a non-gaseous hydrocarbon raw material such as asphalt and a residue oil may be used, for example. Moreover, in the embodiment, fractionation into three fractions of the crude naphtha fraction, the crude intermediate fraction, and the crude wax fraction is performed in the first rectifying column C4, and the crude naphtha fraction and the crude intermediate fraction are hydrorefined in individual steps; however, fractionation into two fractions of a crude light fraction of the crude naphtha fraction and the crude intermediate fraction in combination and the crude wax fraction may be performed, and the crude light fraction may be hydrorefined in one step. Moreover, in the embodiment, the kerosene fraction and the light oil fraction are fractionated as separate fractions in the second rectifying column C12; however, these may be fractionated as one fraction (intermediate fraction).

As described in the embodiment above, part of the crude wax fraction flowed from the column bottom of the first rectifying column C4 and containing the catalyst fine powder may be transferred to the hydrocracker C6 without capturing and removal of the catalyst fine powder. In this case, the catalyst fine powder flowed into the hydrocracker C6 may cause the problem mentioned above such as reduction in activity of the hydrocracking catalyst filled in the hydrocracker C6. The catalyst fine powder, however, are captured and removed from at least part of the crude wax fraction flowed from the column bottom of the first rectifying column C4 and containing the catalyst fine powder in the storage tank T2; accordingly, the amount of the catalyst fine powder to flow into the hydrocracker C6 can be reduced if the same cumulative amount of the oil to flow in the hydrocracker C6 is compared with the case where the catalyst fine powder is not captured and removed. As a result, operation time until the problem described above manifests itself can be increased.

INDUSTRIAL APPLICABILITY

The present invention can provide a method for producing a hydrocarbon oil and a production system that can efficiently suppress the flow of the catalyst fine powder derived from the catalyst to be used for the FT synthesis reaction into the reaction system in the upgrading step of the FT synthetic oil.

REFERENCE SIGNS LIST

T2 ... Storage tank, C4 ... First rectifying column, C6 ... Hydrocracker, C8 ... Intermediate fraction hydrorefining apparatus, C10 ... Naphtha fraction hydrorefining apparatus, C12 ... Second rectifying column, L12, L16 ... Bypass line, L14a, L14b ... Transfer line, 100 ... System for producing hydrocarbon oil.

The invention claimed is:

1. A method for producing a hydrocarbon oil, comprising:
a step of obtaining a hydrocarbon oil containing a catalyst fine powder derived from a catalyst by a Fischer-Tropsch synthesis reaction using a slurry bed reactor holding a slurry containing a liquid hydrocarbon and the catalyst suspended in the liquid hydrocarbon within the slurry bed reactor;
a step of fractionating the hydrocarbon oil into at least one distilled oil and a column bottom oil containing the catalyst fine powder using a rectifying column;
a step of transferring at least part of the column bottom oil to a storage tank, and sedimenting the catalyst fine powder to a bottom of the storage tank to capture the catalyst fine powder; and
a step of transferring a residue of the column bottom oil from the rectifying column to a hydrocracker, and/or transferring a supernatant of the column bottom oil in which the catalyst fine powder is captured in the storage tank from the storage tank to the hydrocracker to hydrocrack the residue of the column bottom oil and/or the supernatant of the column bottom oil using the hydrocracker.

2. The method for producing a hydrocarbon oil according to claim 1, wherein the storage tank comprises a structure for suppressing movement of the catalyst fine powder sedimented to the bottom of the storage tank in the bottom of the storage tank.

* * * * *